United States Patent
Reunanen et al.

(10) Patent No.: US 8,492,586 B2
(45) Date of Patent: Jul. 23, 2013

(54) PROCESS FOR PREPARATION OF FORMATE SALT

(75) Inventors: Jarmo Reunanen, Oulu (FI); Pekka Oinas, Kokkola (FI); Timo Nissinen, Ylojarvi (FI); Esko Tirronen, Espoo (FI)

(73) Assignee: Kemira Oyj, Helsinki (FI)

( * ) Notice: Subject to any disclaimer, the term of this patent is extended or adjusted under 35 U.S.C. 154(b) by 211 days.

(21) Appl. No.: 12/988,998

(22) PCT Filed: Apr. 21, 2009

(86) PCT No.: PCT/FI2009/050312
§ 371 (c)(1),
(2), (4) Date: Dec. 17, 2010

(87) PCT Pub. No.: WO2009/130387
PCT Pub. Date: Oct. 29, 2009

(65) Prior Publication Data
US 2011/0098490 A1    Apr. 28, 2011

(30) Foreign Application Priority Data
Apr. 21, 2008  (FI) ........................... 20085336

(51) Int. Cl.
*C07C 51/00* (2006.01)
*C07C 53/00* (2006.01)
*C07D 307/48* (2006.01)

(52) U.S. Cl.
USPC ............................. 562/609; 562/515; 549/489

(58) Field of Classification Search
USPC ................... 562/609, 515; 549/489
See application file for complete search history.

(56) References Cited

U.S. PATENT DOCUMENTS

| | | | |
|---|---|---|---|
| 2,257,389 | A | 9/1941 | Macallum |
| 2,684,982 | A | 7/1954 | Dunlop |
| 2,813,900 | A | 11/1957 | Dunlop et al. |
| 4,217,460 | A | 8/1980 | Hohenschutz et al. |
| 4,401,514 | A | 8/1983 | Kanzler et al. |
| 4,692,219 | A | 9/1987 | Berg |
| 5,399,751 | A | 3/1995 | Gentry et al. |
| 6,054,611 | A | 4/2000 | Farone et al. |
| 2003/0013926 | A1 | 1/2003 | Saruwatari |
| 2003/0036664 | A1 | 2/2003 | Auer et al. |
| 2005/0172858 | A1* | 8/2005 | Schonherr et al. ....... 106/287.24 |
| 2012/0296118 | A1 | 11/2012 | Heinz et al. |

FOREIGN PATENT DOCUMENTS

| | | |
|---|---|---|
| CN | 1254705 A | 5/2000 |
| CN | 101160279 A | 4/2008 |
| DE | 1518686 | 4/1969 |
| EP | 0038317 A1 | 3/1981 |
| EP | 0365335 B1 | 7/1995 |

(Continued)

OTHER PUBLICATIONS

English Abstract of WO2004006689, 1 pg.

(Continued)

*Primary Examiner* — Taylor Victor Oh
(74) *Attorney, Agent, or Firm* — Thomas Horstemeyer

(57) ABSTRACT

Processes for the recovery of formate salt from biomass and the product obtained thereof generally include subjecting an aqueous liquid mixture containing levulinic acid, formic acid and possibly furfural to a liquid-liquid extraction process, followed by the recovery of the furfural, the formate salt and the levulinic acid or the levulinate salt.

16 Claims, 5 Drawing Sheets

FOREIGN PATENT DOCUMENTS

| | | |
|---|---|---|
| EP | 0873294 B1 | 5/1996 |
| FI | 117633 B | 12/2006 |
| WO | 0146520 A1 | 6/2001 |
| WO | 02053521 A1 | 7/2002 |
| WO | 02053524 A2 | 7/2002 |
| WO | 02053829 A1 | 7/2002 |
| WO | 2004006689 A1 | 1/2004 |
| WO | 2005070867 A1 | 8/2005 |
| WO | 2006108652 A1 | 10/2006 |
| WO | 2009130386 A1 | 10/2009 |
| WO | 2009130387 A2 | 10/2009 |

OTHER PUBLICATIONS

English Abstract of EP0038317, 1 pg.
English Abstract for WO0146520A1, 1 pg.
English Abstract for WO02053521, 1 pg.
English Abstract for WO02053524, 1 pg.
English Abstract for WO2006108652, 1 pg.
Hayes, Daniel J., et al. "The Biofine process—Production of Levulinic Acid, Furfural, and Formic Acid from Lignocellulosic Feedstocks" Biorefineries—Industrial Processes and Products, Status Quo and Future Directions; vol. 1; 2006 Wiley-VCH Verlag GmbH & Co., pp. 139-164.
International Preliminary Report on Patentability for Application PCT/FI2009/050312; Filing Date Apr. 21, 2009, 15 pgs.
Reply to Written Opinion dated May 12, 2010 for Application PCT/FI2009/050312 in regarding to Written Opinion issued Feb. 12, 2010, 4 pgs.
Search Report for Finland Application No. 20085336, dated Oct. 9, 2008, 1 pg.
Written Opinion for Application No. PCT/FI2009/050312; Filing Date: Apr. 21, 2009, 16 pgs.
Abstract for FI117633, 2 pgs.
English Abstract for CN1254705A, Supplied bye espacenet database, http://v3.espacenet.com/publicationDetails/biblio?DB=EPODC&adjacent=true&locale . . . ; 1 pg.
International Preliminary Report on Patentability for Application No. PCT/FI2009/050311, Priority Date: Apr. 21, 2008, date of mailing Apr. 21, 2008, 8 pgs.
Reply to Written Opinion for Application PCT/FI2009/050311, Due date: Feb. 21, 2010, 3 pgs.
Written Opinion of International Searching Authority for Application No. PCT/FI2009/050311; International Filing Date: Apr. 21, 2009; Mail date Jul. 7, 2010, 8 pgs.
Office Action in Corresponding CN Patent Application No. 200980114171.4.

* cited by examiner

PROCESS FOR PREPARATION OF FORMATE SALT

CROSS REFERENCE TO RELATED APPLICATIONS

This is a U.S. national stage of application No. PCT/FI2009/050312, filed on 21 Apr. 2009 Priority under 35 U.S.C. §119(a) and 35 U.S.C. §365(b) is claimed from Finland Patent Application No. 20085336, filed 21 Apr. 2008, the disclosure of which is also incorporated herein by reference.

BACKGROUND

The present invention relates to a process for the preparation of formate salt from biomass and to the product obtained thereof.

Biomass such as pulp, waste paper, paper mill sludge, urban waste paper, agricultural residues, rice straw, woody plant, cotton materials and cellulose fines from papermaking etc. may be reconverted into useful platform chemicals. This requires sufficient economics and reasonable process feasibility for the processes to be used for the recovery of industrially interesting chemicals.

A variety of interesting bulk chemicals is accessible by the acid-catalyzed hydrolysis of biomass such as cellulose which is a natural polymer consisting of glucose units and abundantly available on earth. One attractive option is the conversion of glucose to levulinic acid (IUPAC systematic name: 2-hydroxypropanoic acid i.e. 4-oxopentanoic acid i.e. acetyl propanoic acid) by acid treatment. In the following text, the trivial name levulinic acid is used as the name of this compound. Levulinic acid is a versatile building block for fuel additives, polymers, and resin precursors.

Two different approaches are commonly applied for the acid-catalyzed hydrolysis of cellulose. The first one uses high concentrations of mineral acids (e.g., 15-16 N HCl or 31-70% by weight $H_2SO_4$) as catalysts at low operating temperatures (20-50° C.). The major drawbacks are the high operating cost of acid recovery and the use of expensive construction material for both the hydrolyser and the acid recovery system. The second approach uses highly diluted acids at high operating temperatures (170-240° C.). This method is favoured and research studies applying this approach are abundant.

There are several publications on conversion of biomass to carboxylic acids but none of them simultaneously recover both levulinic acid and formic acid economically and selectively with sufficient purity. Most of the publications disclose methods for converting carbohydrate material to organic acids such as levulinic acid and formic acid, and furfural. A purification process especially to formic acid is not described in the procedures of converting biomass in the literature.

Several publications disclose the separation and recycling of formic acid or more typically carboxylic acids in general, and levulinic acid or furfural from the mixtures thereof. The actual recovery of formic acid as concentrated formic acid or as formate ester or salt as such originating from biomass with suitable purity for further applications could not be found.

In the article of Hayes et al. in Kamm, Gruber, Kamm: Biorefineries—Industrial Processes and Products, Vol. 1, p. 139-164, it is mentioned that the processing of cellulose yields approximately 50% of levulinic acid, 20% of formic acid, and 30% of tars calculated from the mass of 6-carbon sugars. The mass yield of furfural from 5-carbon sugars is approximately 50%. Thus, each ton of levulinic acid produced produces 400 kg of formic acid. There is clearly a need to recover efficiently and simultaneously formic acid parallel to the other platform chemicals.

Formic acid may be recovered in acid form or as a formic acid derivative such as formate ester or salt.

WO2005070867 discloses a reactive extraction method for the recovery of levulinic acid from an aqueous mixture containing e.g. levulinic acid, formic acid and furfural wherein the mixture is first contacted with a liquid esterifying water-immiscible alcohol in the presence of a catalyst at 50 to 250° C. to form esters of levulinic acid and formic acid. These esters remain in organic phase together with the alcohol and furfural. According to the invention, the desired levulinate and all the other compounds can be separated by applying different sequential separation methods, distillations such as e.g., reactive distillation from the organic phase. Formic acid ester is converted to formic acid by acid hydrolysis and separated simultaneously by distillation from the alcohol. This separation process has not been experimentally verified and is known to be very complex. Formic acid is equally obtainable as an ester from the organic phase requiring further processing for the recovery of the pure acid.

In many cases, the carboxylic acids generated as the result of biomass degradation are obtained as dilute aqueous solutions. Distillation is an obvious method to purify isolated substances from aqueous solutions, but distillation as such is not the best option as far as energy-efficiency is considered. Besides, some of the components such as formic acid may form azeotropes with water making the separation into pure components difficult. The separation can be accomplished by arranging several distillation processes and equipment parallel or in series but then the energy cost of separation and equipment will become high. Furthermore, separation into single components is not feasible without using large distillation columns with a high number of separation stages or trays.

Separation of various chemicals may be based on liquid-liquid extraction processes. Even carboxylic acids have been separated from dilute aqueous solutions with extraction solvents insoluble or slightly soluble in water, or with solvent mixtures. However, the efficiency of extraction agents is typically not satisfactory enough to yield pure components.

The solution obtained from biomass degradation, e.g., hydrolysis at elevated temperature and pressure, can contain furfural if the raw material includes pentoses. Furfural in these cases can be converted to its derivatives, such as furfuryl alcohol, methyl furfuryl alcohol, methylfuran, furoic acid, furfurylamine, furan, and their further derivatives. Catalytic hydrogenation of furfural to methyl furan and further into methyltetrahydrofuran or to furfuryl alcohol and further into levulinic acid is mentioned in the literature.

Prior art discloses several ways of recovering industrially valuable components from biomass degradation including furfural or levulinic acid. Aqueous carboxylic acids or mixtures thereof may be separated and/or circulated back to earlier processes stages. Reference is made to patent publications such as WO02053521, WO0146520, EP0038317, and the like.

Neutralization reactions with appropriate alkaline materials are usually applied in order to prepare salt materials from acids. For example, hydrochloric acid and sulphuric acid react with metal oxides, metal hydroxides and metal carbonates to make salts. If the solutions contain several acid components as constituents, the neutralization brings about a mixture of several salts some of which may even precipitate depending on the solubility. The purification or recovery of some specific salt compounds from this kind of multisalt mixtures is very difficult. If multicomponent acid mixtures originating from biomass disintegration processes would be subjected directly to neutralization treatment, multiple salts would be obtained and the recovery of any of the individual acids as pure salt material would be severely complicated and thus uneconomical.

The objective of the present invention is to provide a method for economically and efficiently recovering formic acid in formate salt form from a biomass degradation mixture.

A further objective of the present invention is to provide a method for economically and efficiently recover formic acid in formate salt form together with levulinic acid and optionally furfural from an aqueous mixture of formic acid, levulinic acid and optionally furfural.

Yet, a further object of the present invention is to provide good quality ammonium formate suitable for industrial use.

SUMMARY OF THE INVENTION

The present invention provides an industrially suitable method for the economical and efficient recovery of formic acid in a formate salt form from a mixture that contains other aliphatic acids such as levulinic acid or furfural originating from the reactive treatment of biomass. Since both formic acid and furfural form azeotropes with water, the separation of formic acid as a concentrated platform chemical by distillation has been considered neither easy nor energy-efficient. The method of the invention provides a cost-effective alternative to the typically cost-intensive separation process of formic acid in the form of a good quality formate salt.

The present inventors found that a process by which the distillation and subsequent neutralization of formic acid to give good quality formate salt suitable for industrial use is facilitated when excess water from the dilute liquid mixture originating from the biomass degradation containing formic acid, levulinic acid and furfural is removed first by liquid-liquid extraction and the remaining residual water after the azeotropic distillation of furfural is recycled back to this azeotropic distillation infeed. Especially, it was discovered that prior to formic acid neutralisation into formate salt, in the distillation of furfural azeotrope a certain amount of water is essential to form the furfural-water azeotrope and recycling of water to feed stream after phase separation of the condensate could be utilized to adjust the amount of water required. The separation of essential portion of water from the organic stream directed further to formic acid neutralisation was found useful for the formation of resulting formate salt crystals.

The present invention provides a method for efficient separation and recovery of formic acid as formate salt from an aqueous liquid mixture containing levulinic acid and optionally furfural obtained by biomass degradation.

The benefits of the method described are that good quality formate salt suitable for industrial use is obtained. The obtained formic acid concentration in the intermediate distillate is dependent on the amount of water in the mixture and the location of the withdrawal of the said distillate.

Levulinic acid is recovered as a concentrated acid, preferable in concentrations at least 50% by weight, preferably at least 80% by weight, more preferably at least 85% by weight, most preferably at least 90% by weight, especially such as at least 95% by weight, or as salt thereof, i.e. levulinate. A part of the levulinic acid can be recycled back to the hydrolysis process or to further purification processes.

Furthermore, if the biomass to be degraded contains pentoses, furfural is recovered, typically in parallel to levulinic acid. The recovery is carried out by an azeotropic distillation, such as, for example, distilling a mixture containing about 68% by weight water and about 32% by weight furfural at a pressure of 1 atmospheres (atm) and subsequent phase separation to give concentrated furfural, preferably in a form having a concentration of at least 85% by weight, more preferably at least 90% by weight, most preferably at least 95% by weight, the balance being essentially water.

The present invention further provides good quality crystalline formate salt.

By the term "good quality", it is meant that the obtained formate salt satisfies the criteria for economical and easy preparation, i.e., the obtained crystal particles are easily treated within the recovery process, and they are readily filtered from the mother liquor and resistant to impurity inclusions from the solvent. Furthermore, the resulting crystal powder is freely flowable and shows low dusting performance and low caking tendency. The obtained crystal habit, i.e., the shape and character of the individual crystal or crystal aggregates, induces these good quality properties.

Thus, obtained formate salt is readily usable for its conventional applications and especially suitable for applications requiring good handling properties.

The obtained furfural is commonly used as a solvent in petrochemical refining to extract dienes. Furfural may be used as such or as a derivative like for example furfuryl alcohol, or together with phenol, acetone, or urea to make solid resins. Furfural is also used as a chemical intermediate in the production of furan and tetrahydrofuran.

DETAILED DESCRIPTION OF THE INVENTION

Figure 1:
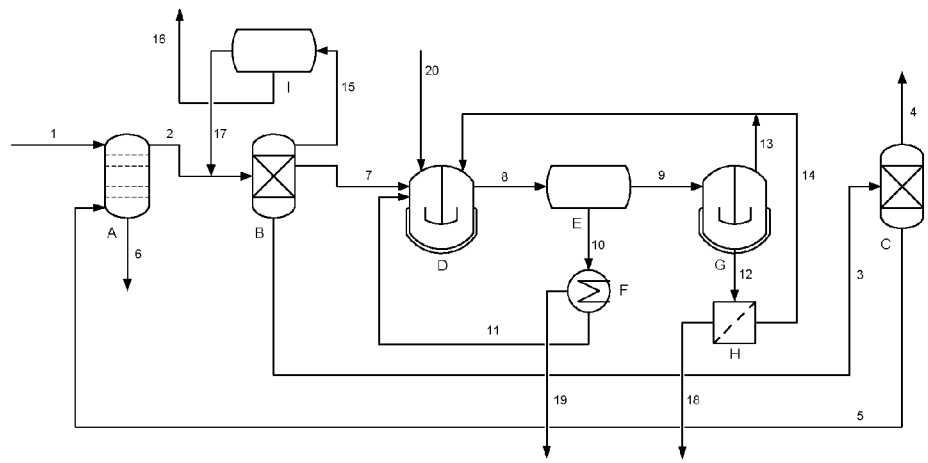
FIG. 1 is a schematic figure of a process for production of formate salt, furfural and levulinic acid wherein extracting agent is used, the boiling point of which is higher than that of levulinic acid.

By the term "biomass" in this invention, it is meant to include pulp, waste paper, paper mill sludge, urban waste paper, agricultural residues, rice straw, woody plant, cotton materials, and cellulose fines from papermaking or any biomaterial which may be converted into formic acid and levulinic acid and optionally furfural. Preferably, carbohydrate containing cellulosic materials such as waste wood, waste paper, primary sludges from paper manufacturing, are used as biomass raw materials. Optionally, the carbohydrate containing cellulosic biomass material contains components that in biomaterial hydrolysis are at least partly converted into furfural, such as pentoses.

This biomass may be degraded or treated by any known method to provide a mixture containing suitable precursors for formic acid and levulinic acid and optionally furfural. Preferably, the mixture to be treated by the method according to the invention is obtained by acidic hydrolysis since this process has proved to be a practical solution and technologically feasible compared to, for example, biological or bacterial treatments. The mixture to be treated can be obtained by inorganic acid-hydrolysis treatment at elevated operating temperatures and corresponding pressures, preferably at a temperature from 150 to 250° C. and at a pressure from 10 to 40 bar.

By the term "mixture" in the present invention, it is meant an aqueous liquid mixture. This mixture is suitable for further processing by the method of the invention described below. Preferably, this mixture is suitable for liquid-liquid extraction process by conventional liquid-liquid extraction means allowing the presence of some solids, preferably less than 5%, more preferably less than 1% by weight, but wherein the amount of solids needs to be low enough for not disturbing the extraction process. This mixture preferably includes formic acid up to 10% by weight, preferably, levulinic acid up to 15% by weight and optionally furfural up to 10% by weight. The mixture may further include inorganic acid(s) and/or acetic acid. Acetic acid may be formed in the degradation of hemicellulose through pentosan sugar fraction. More preferred concentrations are for formic acid from 1 to 5% by weight, for levulinic acid from 3 to 8% by weight, and optionally for furfural from 1 to 5% by weight and optionally for inorganic acids up to 10%, preferably from 1 to 5% by weight, the balance being water.

The method provided by the present invention comprises separating and recovering at least formate salt from an aqueous liquid mixture containing levulinic acid and optionally furfural obtained by biomass degradation by using at least the following steps:

i. The mixture containing formic acid and levulinic acid and optionally furfural is subjected to liquid-liquid extraction by employing an extracting agent whereby an organic phase comprising the extracting agent, formic acid, levulinic acid and optionally furfural and an aqueous phase comprising essentially water, preferably further containing inorganic acid(s), are obtained. The aqueous phase is separated and removed from the organic phase by gravitation.

ii Said organic phase comprising formic acid and levulinic acid and optionally furfural obtained from step i after the removal of the aqueous phase is subjected to a distillation step for optionally separating and recovering furfural and separating formic acid from said organic phase. In this distillation step furfural is optionally separated and recovered from the top of the distillation column. Levulinic acid exits from the bottom of said distillation column. Formic acid is separated from the middle part of said distillation column.

iii. Formic acid is recovered in a form of formate salt after step ii distillation by subsequent neutralisation.

iv. Levulinic acid or levulinate salt is recovered after step ii distillation from the organic phase. The recovery is realised either by performing a second distillation step to produce levulinic acid or by neutralisation into levulinate salt.

Preferably, the method according to the invention comprises a further recycling step v of recovering and recycling said extracting agent which is still present in the organic phase after the removal of formic acid, levulinic acid and optionally furfural. The extracting agent is recycled back to the extraction step i as infeed. The extracting agent may be obtained from the second distillation in step iv either as the bottom product (for example, FIG. 1, flow 5) or as the condensed overhead product (FIG. 2, flow 5). Alternatively, the extracting agent is obtained from the decantation tank in step iv as the upper product (see FIG. 3, flow 5) or as the filtrate from filtration and further from decantation (see FIG. 4, flow 23 and flow 5).

Preferably, the step ii comprises a further recycling step vi wherein the residual aqueous component (FIG. 1, flow 17) from the separation of furfural is recirculated back to step ii infeed.

Preferably, the method according to the invention comprises a further recycling step vii wherein the aqueous phase (FIG. 1, flow 6) separated in step i is recycled back to the previous processes for biomass degradation. This aqueous phase may be recycled back to, for example, the biomass acid-hydrolysis. The aqueous phase to be recycled may comprise still some formic acid, levulinic acid and furfural, if present in the mixture of step i. Most preferably, the aqueous phase to be recycled contains essentially no organic acids. The aqueous phase comprises preferably at least one inorganic acid necessary in the acid-hydrolysis.

Liquid-liquid extraction is a process that separates components based upon chemical differences rather than differences in physical properties. Extraction involves the contacting of a solution with an extracting agent, another reagent and/or solvent that is immiscible with the original one. The solutes contained in the solution are soluble in the extracting agent. Two phases are formed after the addition of the extracting agent, due to the differences in densities between the phases. The extracting agent is chosen in such a way that the solute in the solution has more affinity towards the added extracting agent. Therefore, mass transfer of the solute from the solution to the extracting agent occurs. Liquid-liquid extraction was found useful in removing most of the water from the dilute acidic solution forming the aqueous liquid mixture of the present invention.

In the first step, the mixture originating from the biomass degradation (FIG. 1, flow 1) comprising formic acid, levulinic acid, water and optionally furfural is directed to conventional liquid-liquid extraction means F 1, A). In the selection of appropriate equipment for liquid-liquid extraction, it is preferred that the contacting area of mass transfer is maximized and the flows of the separated phases are properly adjusted for maximum solute recovery. The equipment preferred for liquid-liquid extraction is the following: First, contacting columns can be used for most liquid-liquid extraction systems. In these columns, the internal packings, trays, or sprays increase the surface area for the two liquid phases to intermingle. This also allows for a longer flow path that the solution can travel through in the contacting column. In the selection of the column packing, it is necessary to select such a material that is best wetted by the continuous phase. The flow in a column should be counter-current. Second, centrifugal contractors are preferred for systems for liquid-liquid extractions where the density difference between the phases is small, preferably less than 4%. This type of system should be utilized in processes requiring multiple equilibrium stages. Third, mixer-settlers with one equilibrium stage in each cell usually requiring a large-volume vessel and a high liquid demand may be utilized as well.

Whatever the selection of the equipment is, operating variables such as operating temperature, operating pressure, feed flow rates and compositions and the temperature and pressure of the entering streams in an liquid-liquid extraction process are to be assigned. The pressure and temperature must be selected so that all components remain in the liquid phase. Preferably, the pressure in the liquid-liquid extraction is less than 3 bar, more preferably ambient pressure is used such as 1 bar, and the temperature is preferably less than 100° C., more preferably from 20 to 100° C., most preferably from 30 to 60° C.

The mixture (FIG. 1, flow 1) introduced to step i containing formic acid, levulinic acid, water and preferably comprising further at least one inorganic acid, and optionally furfural is subjected to liquid-liquid-extraction by employing a water-immiscible or slightly water-soluble organic extracting agent into which the organic compounds are transferred by dissolution. As the result, two separate phases with different densities are obtained; namely the organic phase comprising of the extracting agent, formic acid, levulinic acid and optionally furfural, and an aqueous phase comprising essentially of water, preferably comprising further at least one inorganic acid, are obtained.

The ratio of the aqueous liquid mixture to the extracting agent to be fed into the extraction step i should be 1 or more, preferably 2 or more, more preferably 4 or more, most preferably about 10.

The inorganic acid(s) in the mixture may originate from the previous biomass degradation processes such as acid hydrolysis. The amount of inorganic acid in the mixture is preferably up to 10% by weight, more preferably from 1 to 5%. Preferably this inorganic acid is sulphuric acid. The acid is separated in the extraction step i and essentially all of it, preferably at least 95%, remains in the separated aqueous phase. This acid may be recycled back to, for example, the acid hydrolysis together with the aqueous phase. It was found that the presence of dense inorganic acid may even facilitate the separation in the liquid-liquid extraction equipment.

The mixture to be subjected to extraction in step i may further contain acetic acid less than 10% in weight, preferably less than 5% in weight, more preferably from 0 to 3% by weight, depending on the process used for the biomass degradation. Most of acetic acid will be transferred into the organic phase in liquid-liquid extraction, preferably less than 10% by weight of the originally present amount in the mixture remains in the aqueous phase.

The extracting agent according to the invention comprises at least one extracting solvent and/or at least one extracting reagent. The selection of the extraction reagent depends on separation efficiency due to different densities between the organic and aqueous phase, miscibility of the phases, dissolution of the solutes to the extracting agent depending on the polarity measured by dipole moment and dielectric constant. The boiling point of the extracting agent may be lower or higher than that of levulinic acid. The extracting agent may thus be pure extracting reagent, a mixture of extracting reagents, an effective extracting reagent in solvent or in solvent mixture, several extracting reagents in solvent or in solvent mixture. All commonly known extraction agents or their combinations and like agents used in liquid-liquid extraction satisfying the above mentioned criteria may be applied. As an example, suitable extraction agents may be found for example in Handbook of Solvent Extraction by Lo and Baird (1991), and especially for carboxylic acid extraction from aqueous solutions in U.S. Pat. No. 5,399,751, U.S. Pat. No. 4,401,514, US 2003/0036664, U.S. Pat. No. 4,217,460, WO02/053524, and especially for levulinic acid extraction in Shil'nikova and Sharkov, Angew. Chem. Chem. Fabrik (1965), 14, 147-51.

According to the invention, the aqueous acidic solution from biomass disintegration can be extracted with an extracting agent selected form the group of amines, amides, phosphine oxides, fatty acids or their esters, fatty alcohols, ketones, ethers, organophosphates and substituted urea derivatives. Preferred extracting agents are tertiary amines, secondary or tertiary amides, tertiary phosphine oxides, tertiary phosphates, $C_5$-$C_{12}$ fatty acids, $C_8$-$C_{12}$ fatty alcohols and alkyl urea derivatives. More preferred extracting agents are tertiary octyl-, hexyl- or octyl-hexyl-phosphine oxides such as Cyanex 923, or mixtures thereof, dibutyl amine, trioctyl phosphate, methyl ethyl ketone, octanol, and tetrabutyl urea. In a preferred embodiment, extracting agents functioning as solvents are long chain aliphatic alkanes. More preferred extracting agents functioning as solvents are aliphatic hydrocarbons or aliphatic hydrocarbons with aromatic or aliphatic substituents or mixtures thereof, such as decane or kerosene or diphenylalkene.

It is preferred to carry out the extraction with a minimum amount of organic extracting agent since the higher the amounts of solutions in extraction and distillation the larger the equipment sizes and higher capital costs become. It is noted that the material requirements for the equipment are high due to the corrosive environment caused by formic and sulphuric acid. Materials, such as coated or cladded steels, zirconium, titanium and duplex are preferred. Furthermore, the lower the volume of solutions the lower the energy demand in distillation.

Any insoluble solids in the mixture to be extracted originating from the previous processes, for example tar, remain in the heavier aqueous phase.

In a preferred embodiment in the extraction step i, it is not required to remove all possible furfural, formic acid and levulinic acid because those chemicals may be recirculated in the aqueous phase back to previous process stages for biomass degradation, such as hydrolysis step. The aqueous phase to be recycled back comprises preferably up to 25% by weight furfural and up to 5% by weight levulinic acid compared to their infeed amount into the extraction step i, most preferably aqueous phase to be recycled back comprises essentially no furfural or levulinic acid. Since it is not necessary to obtain full recovery of chemicals in the liquid-liquid extraction, it is possible to reduce equipment and reagent costs and thus investment and operating costs.

In the liquid-liquid extraction step i, water, preferably 70%, more preferably 90%, most preferably 95% by weight, from the infeed aqueous liquid mixture is transferred into the aqueous phase.

Figure 2:
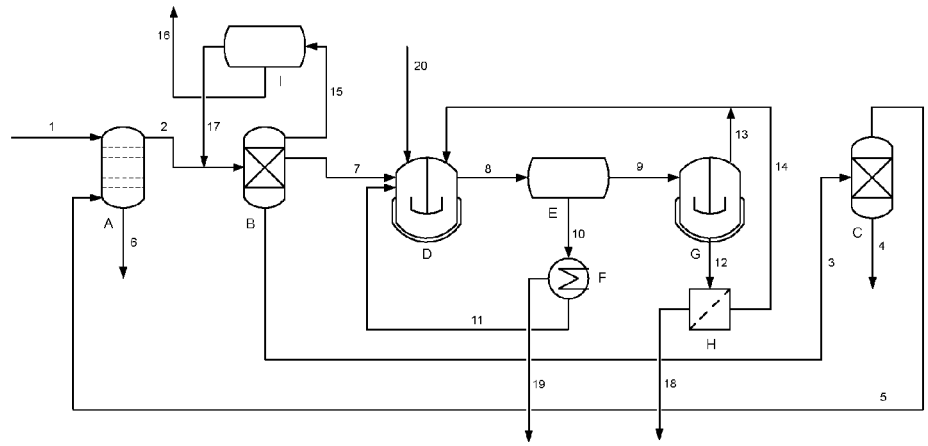
FIG. 2 is a schematic figure of a process for production of formate salt, furfural and levulinic acid, wherein an extracting agent is used, the boiling point of which is lower than that of levulinic acid.

As this aqueous phase is circulated back to biomass degradation such as hydrolysis, the organic phase (FIG. 1, flow 2) still containing some water is subjected to step ii (FIG. 1, B).

In a preferred embodiment the organic phase from step i contains furfural. This furfural is separated and recovered in step ii. Furfural to be recovered is separated by distillation wherein furfural and water are separated from the organic phase as furfural-water azeotrope vapour in the overhead of distillation column (FIGS. 1 and 2, B). The organic phase infeed (FIG. 1, flow 2) into furfural distillation step ii comprises water preferably not more than 5%, more preferably from 1 to 5%, most preferably from 1 to 4% by weight. The presence of this water is advantageous for the complete depletion of furfural from the organic phase. If there is not enough water in the infeed of this distillation step additional water infeed may be required.

The vaporized azeotropic furfural-water mixture is condensed and due to different densities two immiscible phases are formed in a decantation vessel or phase separation tank (FIG. 1, I). The aqueous phase is separated from the organic phase as lighter phase by gravitation. Furfural (FIG. 1, flow 16) is recovered from the organic phase in a form having a concentration of at least 80% by weight. At room temperature the furfural organic phase contains preferably at least 85% by weight of furfural, more preferably at least 90% by weight, most preferably 95% by weight, the balance being essentially water.

The aqueous phase from the decantation vessel contains preferably not more than 10% by weight furfural, the balance being essentially water. This aqueous phase (FIG. 1, flow 17) is preferably recycled and combined to the feed stream (FIG. 1, flow 2) prior to azeotropic distillation of furfural and thus adjusting the water-to-furfural ratio which is important for the formation of furfural-water azeotrope and efficient furfural separation.

In the step ii, formic acid is separated from the middle part of the distillation column from said organic phase containing formic acid, levulinic acid and optionally furfural entering the distillation column.

Formic acid rich, water and furfural containing stream is separated from furfural distillation column as a side stream (FIG. 1, low 7). This stream preferably comprises 10 to 80% by weight formic acid, more preferably 40 to 80%. The furfural content of this stream is less than 40% by weight, preferably less than 20%, more preferably less than 10%. This formic acid rich portion is subsequently directed to step iii for recovery. The amount of water in this distillation affects the concentrations of furfural in both the formic acid rich side stream and furfural rich top distillate.

Preferably, the furfural-water azeotropic distillation is performed in reduced pressure. More preferably this distillation is carried out under reduced pressure of less than 500 mbar, most preferably between 100 to 300 mbar, since the mass fraction of furfural in the azeotrope is increased as pressure is decreased and the boiling point of the azeotrope is decreased.

In the step ii, the residual heavy bottom flow rich in levulinic acid and extracting agent is separated from the distillation column. This flow is directed further into step iv to a second distillation column (FIG. 1, C) wherein levulinic acid is recovered from this mixture of extracting agent and levulinic acid.

Figure 5:
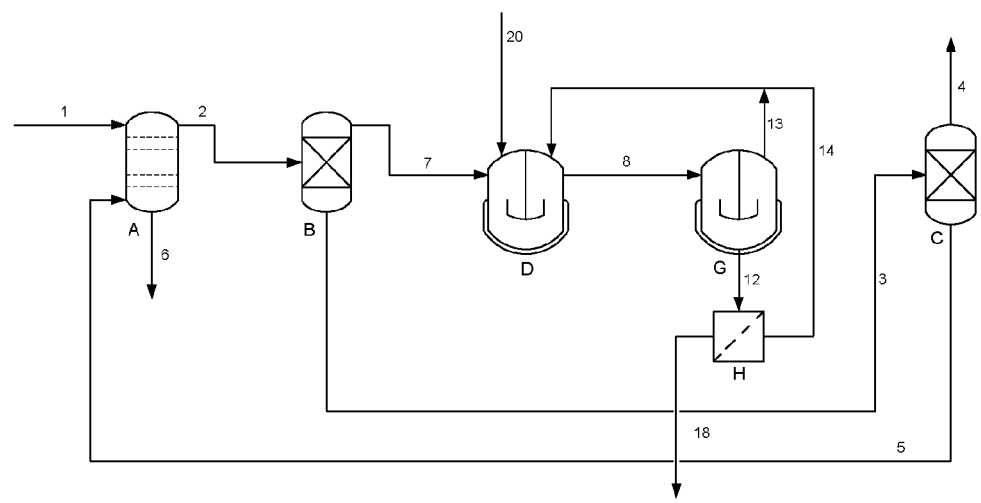
FIG. 5 is a schematic figure of a process for production of formate salt and levulinic acid in the absence of furfural, wherein an extracting agent is used, the boiling point of which is higher than that of levulinic acid.
Figure 6:
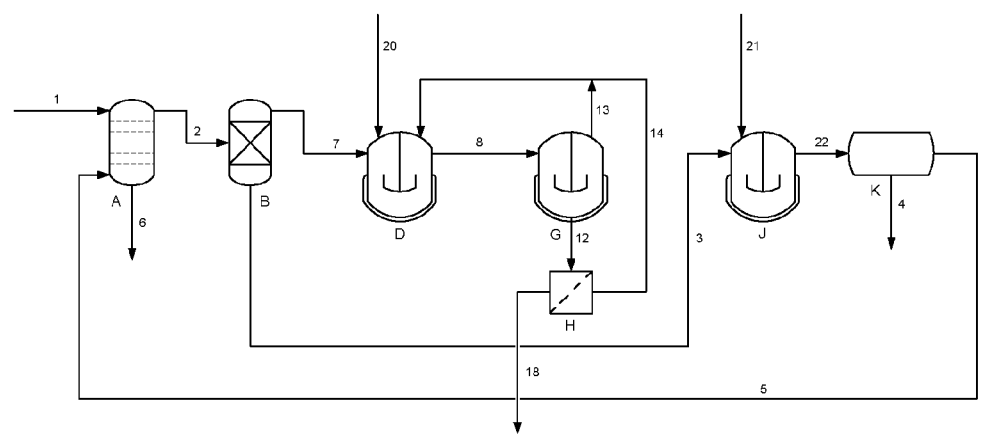
FIG. 6 is a schematic figure of a process for production of formate salt and levulinic acid in the absence of furfural, wherein extracting agent is separated by decantation from the levulinate salt solution.

In an other embodiment if the organic phase entering step ii distillation does not comprise any furfural the distillation may yet be performed equally to the embodiments including furfural. Formic acid rich phase (FIGS. 5 and 6, flow 7) is withdrawn from the distillation column in the top part of the column and levulinic acid rich phase from the bottom (FIGS. 5 and 6, flow 3).

In the step iii formic acid is separated from the formic acid rich stream (FIG. 1, flow 7) as formate salt preferably by neutralization with a base chemical. A suitable base chemical contains preferably basic metal cation(s) or ammonium ion, more preferably metal cation(s) from group I A or II A of the periodic table of elements, even more preferably Na, K, Ca, Mg and/or ammonium ion.

The base chemical and formic acid react to formate salt. Depending on the used base chemical and the concentration of the reactants the formate salt either remains dissolved or precipitates as a solid. Preferably, formate salt is in dissolved state. The neutralization reaction is performed in a reaction vessel, in a mixing tank or in the pipe reactor equipped with static mixers (FIG. 1, D). The base chemical which contains appropriate amount of water depending on the solubility of the base chemical and the product is fed separately (FIG. 1, flow 20) into the reaction vessel. The neutral formate containing mixture (FIG. 1, flow 8) from the neutralization reactor is led to separation, preferably in a decantation vessel (FIG. 1, E) or phase separation tank. In the decantation vessel phase separation occurs most advantageously, if the two-phase mixture contains enough furfural, preferably this amount is more than 4% by weight, more preferably more than 5%, and most preferably more than 8% depending on the amount of other dissolved species.

In a preferred embodiment the aqueous formate rich stream (FIG. 1, flow 9) is led into a crystallizer (FIG. 1, G). This crystalliser type may be cooling crystallizer or preferably evaporative vacuum crystallizer. In this crystallizer formate salt will be generated. The formed slurry (FIG. 1, flow 12) is led into a solid-liquid separating equipment (FIG. 1, H) which is preferably a pressure or vacuum filter or a centrifuge. The filtered crystals are collected as the end product (FIG. 1, flow 18). Only minor amount of furfural, preferably less than 1000 ppm, more preferably less than 200 ppm and most preferable less than 100 ppm, remains in this stream consisting of the formate salt. The filtrate (FIG. 1, flow 14) is preferably led back to the neutralization reaction vessel, or to dissolution or dilution of the alkaline neutralizing chemical employed. Evaporated water (FIG. 1, flow 13) is preferably led back from the crystallizer to the neutralization, or to dissolution or dilution the alkaline neutralizing chemical employed. The furfural containing phase in decantation vessel is preferably conducted into the film evaporator (FIG. 1, F) in which furfural is evaporated. Furfural is collected as furfural end product and is led (FIG. 1, flow 19) to storage. Furfural present in the bottom of the evaporator among formate salt and not evaporated is forwarded (FIG. 1, flow 11) back to the neutralization vessel (FIG. 1, D).

The distillation column bottom product (FIG. 1, flow 3) from the step ii comprising levulinic acid and the extracting agent and optionally acetic acid if it is present in the infeed mixture, is passed to a second distillation column or evaporator (FIG. 1, C) in step iv for levulinic acid recovery.

In the step iv, levulinic acid is separated from the organic phase preferably by distillation. Levulinic acid is separated from the remaining extracting agent and any impurities still dissolved therein as overhead vapour (FIG. 1, flow 4) and the vapour is condensed to give liquid levulinic acid or liquid bottom product (FIG. 2, flow 4) depending on the boiling point difference between levulinic acid and the selected extracting agent.

In the embodiment according to FIG. 1, levulinic acid with a lower boiling point compared to the extracting agent and thus being more volatile is obtained as the overhead product. The extracting agent remains in the bottom product and is recycled back to the liquid-liquid extraction of step i. If acetic acid is present in the feed mixture it will be co-distilled with levulinic acid as an overhead product. Subsequently, acetic acid may be separated together with levulinic acid and further separated from levulinic acid by a further distillation step. As it is preferred to recycle the extracting reagent as a pure product back to the liquid-liquid extraction step i this case is preferred.

In an embodiment according to FIG. 2, the extraction reagent having a lower boiling point and higher volatility than levulinic acid is distilled as an overhead product. This overhead product is recycled back to liquid-liquid extraction process. Levulinic acid is recovered as the bottom product. If acetic acid is present it may be separated with the extraction reagent and may be recycled back to extraction step i.

Alternatively, in the step iv, levulinic acid is separated from the organic phase preferably by neutralization with a base. This base comprises a basic metallic cation or ammonium ion, preferably said cation is from group I A or II A of the periodic table of elements, more preferably said cation is Na, K, Ca, Mg or ammonium which compounds have high solubility at high temperatures and show good performance in crystallisation and/or separation processes. Especially ammonium and potassium cations are preferred due to low cost and favourable residues such as ammonium sulphate and potassium sulphate, respectively. The base reacts with levulinic acid to produce the levulinate salt. Preferably, the process is a continuous process.

FIGS. 1-6 show examples of the different possible embodiments according to the present invention.

Figure 3:
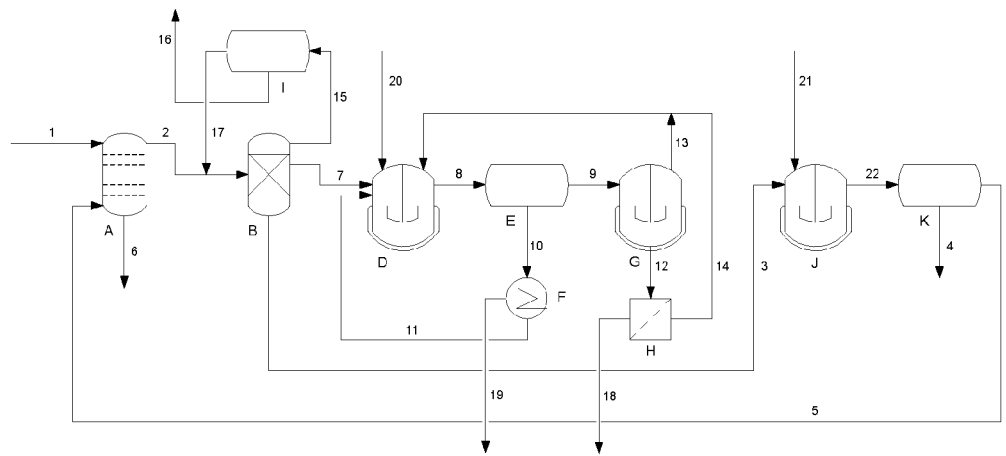
FIG. 3 is a schematic figure of a process for production of formate salt, furfural and levulinate salt, wherein extracting agent is separated by decantation from the levulinate salt solution.

Depending on the choice of the base, concentrations and/or reactants the formed levulinate either remains in solution as dissolved species or it precipitates into a solid. The neutralization reaction takes place in a reaction vessel, preferably in a mixing tank or in a pipe reactor equipped with static mixers (FIG. 3, J) or the like. An aqueous base solution is fed separately into the reaction vessel (FIG. 3, flow 21). If levulinate salt remains dissolved the resulting neutral mixture (FIG. 3, flow 22) from the reaction vessel is preferably led to decantation vessel or phase separation tank (FIG. 3, K) wherein phase separation occurs. Levulinate salt remains in the aqueous phase and is led out from the process and obtained as the product (FIG. 3, flow 4). The extracting agent (FIG. 3, flow 5) which contains up to 10% by weight, preferably up to 5%, more preferably from 1 to 5% water is led back to the extraction vessel (FIG. 3, A). Only a minor amount, preferably less than 1% by weight, of levulinate salt is present in this stream.

Figure 4:
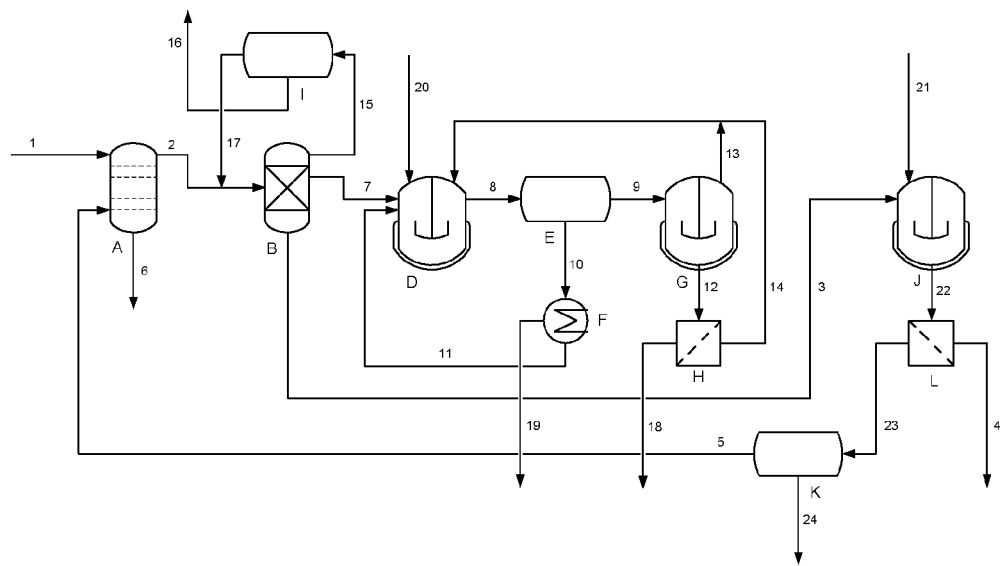
FIG. 4 is a schematic figure of a process for production of formate salt, furfural and levulinate salt, wherein an extracting agent is separated by filtration from the levulinate salt solution.

In an other embodiment of the invention the neutral mixture (FIG. 4, flow 22) from the neutralization reactor (FIG. 4, J) is led in to the filtration equipment or in to the centrifuge (FIG. 4, L) if the levulinate precipitates into solid phase. In the filtration equipment levulinate salt is separated and collected as the product (FIG. 4, flow 4). Filtrate (FIG. 4, flow 23) is led to the decantation vessel (FIG. 4, K) in which phase separation occurs. The extracting agent (FIG. 4, flow 5) that contains up to 10% by weight, preferably up to 5% more preferably from 1 to 5%, water is led back to extraction vessel (FIG. 4, A). Only minor amount of levulinate, preferably less than 1% by weight, remains in this stream (FIG. 4, flow 5). Water rich aqueous phase (FIG. 4, flow 24) is led out for further use.

If the purities of the obtained products are not sufficient, auxiliary purification processes may be applied. These processes include conventional methods of distillation, stripping, adsorption, evaporation, crystallization and filtration.

There may be other methods or arrangements of implementation of the conceptual processing system and equipment before distillation steps than the one applied here which are obvious modifications of the present invention for those skilled in the art and thus included in the present invention.

According to one embodiment of the present invention good quality formate crystals are obtained by the method. This formate salt product produced by the above described method is especially suitable for industrial use.

The present invention further provides good quality formate crystals. It was surprisingly observed that furfural as an ingredient in the crystallization solution has a positive effect on crystal habit.

It is known that certain chemical compounds added to the crystallization mixture may have dramatic effects on the crystallization and crystal habits, as well. By using additives, different crystal forms may appear. This is due to the fact that the growth rates of certain crystal faces can be retarded by adsorption of additives on the crystals surface. Since the molecules have a different orientation at the different crystal faces, the additives may affect differently on the growth rate of different faces. Thus, by selecting the additives properly, the growth rates can be affected in such a way that the morphology of the crystal changes. Besides, additives can affect the dissolution rates by changing the shape of the crystals and suitable additives enhance the wettability through hydrophilization of the crystal surface.

Figure 7:
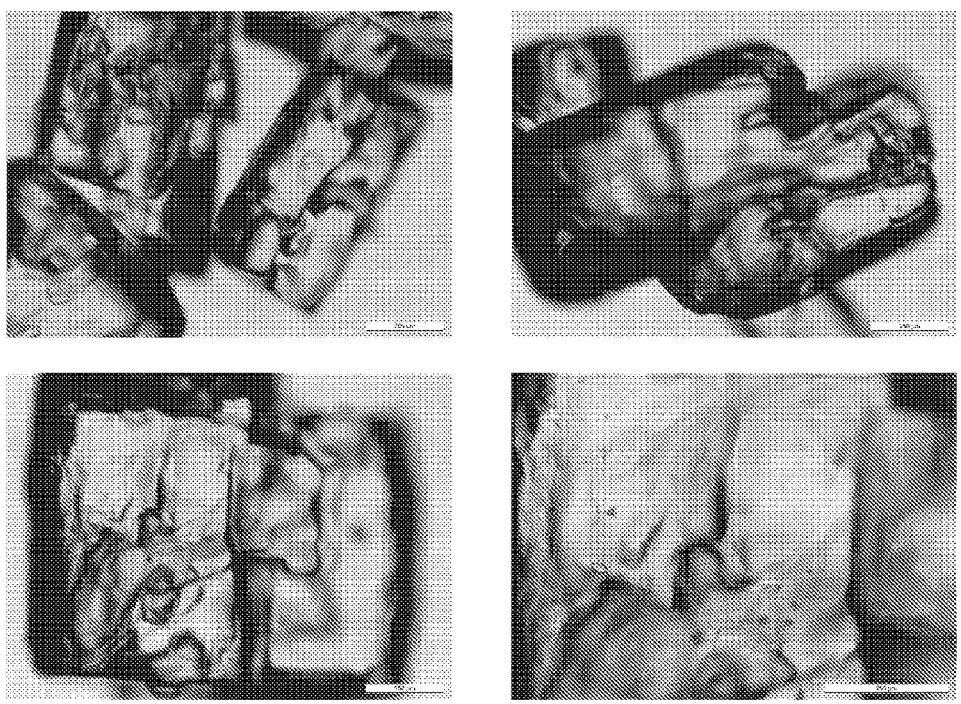
FIG. 7 shows Ammonium formate crystals obtained without furfural. The white dimension bars in the figures top right and left and bottom left indicate a length of 250 μm and the white dimension bar in the figure bottom right indicates a length of 200 μm.
Figure 8:
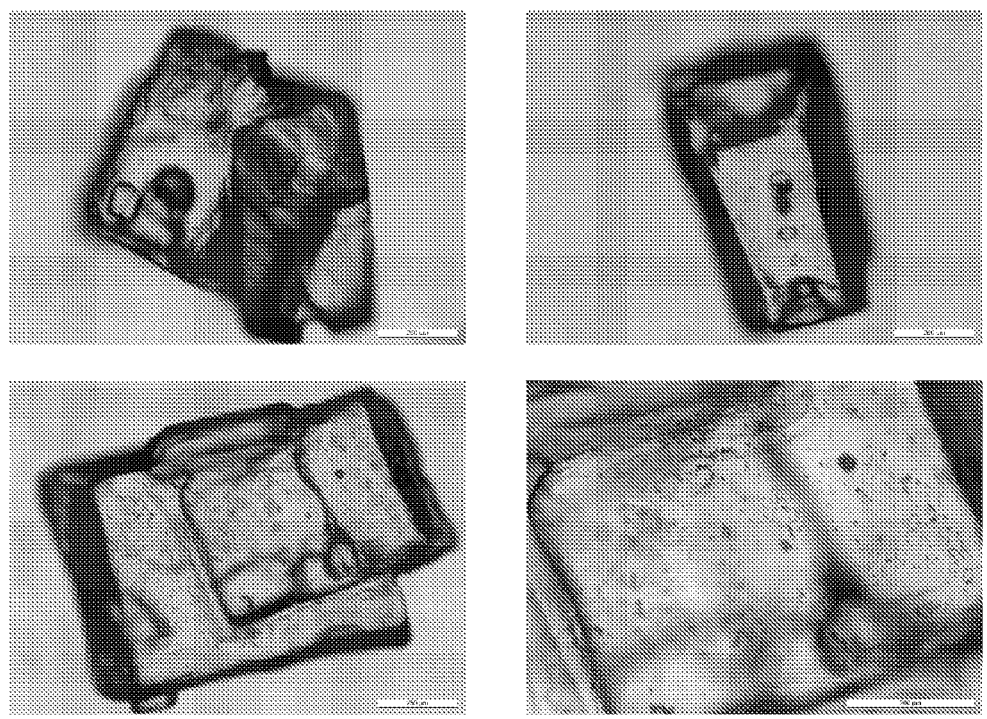
FIG. 8 shows Ammonium formate crystals obtained by neutralization with aqueous ammonia. The white dimension bars in the figures top right and left and bottom left indicate a length of 250 μm and the white dimension bar in the figure bottom right indicates a length of 200 μm.

During the separation and recovery experiments of present invention the inventors realized that good crystal quality formate salts were obtained by having furfural in the crystallization mixture compared to the case where furfural was not present. This is observed from the shape of ammonium formate crystals obtained as shown in FIGS. 7 and 8. The amount of furfural is preferably at least 0.01% by weight, more preferably from 0.1 to 0.5% by weight, or even up to 1% by weight. A yet larger amount of furfural is possible but not desired for practical reasons such as further processing and recycling of fluids.

The equivalent spherical diameter (defined by the diameter of the corresponding spherical particle having the same volume) of the crystal particles is at least 100 µm, preferably at least 150 µm, more preferably at least 200 µm. These formate salt particles, preferably ammonium formate particles, have a regular shape, the sphericity $\Psi$ is larger that 0.5, preferably larger than 0.64 and most preferably 0.81. The sphericity $\Psi$ is defined by $$\Psi = \frac{(6\alpha/\pi)^{\frac{2}{3}}}{\beta/\pi},$$

where $$\alpha = \frac{V_p}{L^3}$$

is the volume shape factor and $$\beta = \frac{A_p}{L^2}$$

is the surface shape factor.

The crystals of this size and regularity provide good filterability and good flow properties due to absence of small particles. Further, the regular shape of the crystals give rise to regular growth of crystals and the exclusion of agglomeration and possible inclusions in particulate material which in turn facilitate the removal of mother liquor and its dissolved impurities giving rise to purer product crystals. The large crystal size leads also to decreased dusting properties. Larger crystals with smaller external surface area result in decreased hygroscopicity and consequently lesser caking aptitude in storage. All these observations are indications of crystalline material with good quality and high purity.

According to a preferred embodiment of the present invention good quality formate crystals are obtained by the method of claim 1 which have an equivalent spherical diameter of the crystal particles of at least 100 µm, preferably at least 150 µm, more preferably at least 200 μm, and a sphericity of 0.5, preferably larger than 0.64 and most preferably 0.81.

In a other preferred embodiment of the present invention ammonium formate crystals are produced by the above described method which preferably have an average equivalent diameter of the crystal particles of at least 100 μm, preferably at least 150 μm, more preferably at least 200 μm, and a regular shape with a ratio of the crystal particle length to it's width of about 2. An example of these crystals is shown in FIG. 8.

Depending on the operating parameters, some furfural may be remaining in the formate salt product. Preferably the amount of furfural is less than 1000 ppm, more preferably less than 200 ppm, more preferably less than 100 ppm. The raw material of the biomass process may include some volatile wood decomposition compounds that might produce minor amounts of impurities, preferably less than 0.1% by weight, more preferably less than 0.05% by weight, most preferably 0.01% in the final formate product. No traces of levulinate could be detected from the products.

It is anticipated without being bound to any theory that the presence of furfural during the manufacture of the formate salt has surprisingly a favorable effect on the crystal formation and shape of the product and thus enhances the quality of the product obtained by this method.

Different types of distillation column systems, such as various sequences of columns and modified column internals such as divided wall columns could be used to enhance the energy-efficiency of distillation.

EXAMPLES

The invention will be further illustrated by means of the following non-limiting examples.

Example 1

A liquid mixture of 35.0 grams (g) formic acid, 55.0 g furfural, and 10.0 g water was put in a separation funnel. A suspension of 25.05 g CaOH and 100.0 g water was added in to the same separation funnel. The mixture was shaken vigorously for 5 minutes (min.). The solid material was separated using a büchner filter funnel. The filtrate which had two layers was collected in to the separating funnel. Separation into organic and aqueous phase took place after letting the filtrate stand for 5 min. and the two phases were removed into separate vessels. Samples for the analysis were taken from both phases. After the sampling, the aqueous phase was transferred to rotavapor and the liquid was evaporated. The remained solid material was collected and analysed. The analysed results are shown in Table 1.

TABLE 1

|  | Calcium formate, wieght percent (w-%) | Furfural, w-% | Water, w-% |
|---|---|---|---|
| Aqueous phase | 3.2 | 5.6 | 92.7 |
| Organic phase | 2.1 | 85.6 | 4.8 |
| Solid from filter | 94.4 | 0.6 |  |
| Solid from evaporator |  | <0.02 |  |

Example 2

A liquid mixture of 60.02 g formic acid, 60.0 g furfural, and 30.0 g water was put in a glass vessel. A mixture of 51.51 g NaOH and 206.05 g water was added in to the same glass vessel by a pump within a period of 50 min. The mixture was agitated by a magnetic stirrer during alkali addition. The mixture was poured into a separation funnel. Separation into organic and aqueous phase took place after letting the filtrate stand for 5 min. and the two phases were removed into separate vessels. Samples for the analysis were taken from both phases. The analysed results are shown in Table 2.

TABLE 2

|  | Sodium formate, w-% | Furfural, w-% | Water, w-% |
|---|---|---|---|
| Aqueous phase | 24.8 | 2.2 | 73.0 |
| Organic phase | 0.3 |  |  |

Example 3

A liquid mixture of 60.01 g formic acid, 59.99 g furfural, and 30.0 g water was put in a glass vessel. A mixture of 50.70 g NaOH and 76.05 g water was added in to the same glass vessel by a pump within a period of 50 min. The mixture was agitated by a magnetic stirrer during alkali addition. The mixture was poured into a separation funnel. Separation into organic and aqueous phase took place after letting the filtrate stand for 5 min. and the two phases were removed into separate vessels. Samples for the analysis were taken from both phases. The analysed results are shown in Table 3.

TABLE 3

|  | Sodium formate, w-% | Furfural, w-% | Water, w-% |
|---|---|---|---|
| Aqueous phase | 40.0 | 0.9 | 59.1 |
| Organic phase | 0.3 |  |  |

Example 4

A liquid mixture of 60.02 g formic acid, 60.00 g furfural, and 30.0 g water was put in a glass vessel. A mixture of 70.93 g KOH and 283.72 g water was added in to the same glass vessel by a pump within a period of 70 min. The mixture was agitated by a magnetic stirrer during alkali addition. The mixture was poured into a separation funnel. Separation into organic and aqueous phase took place after letting the filtrate stand for 5 min. and the two phases were removed into separate vessels. Samples for the analysis were taken from both phases. The analysed results are shown in Table 4.

TABLE 4

|  | Potassium formate, w-% | Furfural, w-% | Water, w-% |
|---|---|---|---|
| Aqueous phase | 20.9 | 4.7 | 74.4 |
| Organic phase | 1.0 |  |  |

Example 5

A liquid mixture of 60.01 g formic acid, 60.00 g furfural, and 30.0 g water was put in a glass vessel. A mixture of 69.36 g KOH and 104.04 g water was added in to the same glass vessel by a pump within a period of 70 min. The mixture was agitated by a magnetic stirrer during alkali addition. The mixture was poured into a separation funnel. Separation into organic and aqueous phase took place after letting the filtrate stand for 5 min. and the two phases were removed into separate vessels. Samples for the analysis were taken from both phases. The analysed results are shown in Table 5.

TABLE 5

|  | Potassium formate, w-% | Furfural, w-% | Water, w-% |
| --- | --- | --- | --- |
| Aqueous phase | 36.0 | 3.2 | 60.8 |
| Organic phase |  | 1.4 |  |

Example 6

A liquid mixture of 60.00 g formic acid, 60.00 g furfural, and 30.0 g water was put in a glass vessel. 221.60 g of 10 w-% aqueous ammonia was added into the same glass vessel by a pump within a period of 30 min. The mixture was agitated by a magnetic stirrer during alkali addition. The mixture was poured into a separation funnel. Separation into organic and aqueous phase took place after letting to stand 5 min. and the two phases were removed into separate vessels. Samples for the analysis were taken from both phases. The analysed results are shown in Table 6.

TABLE 6

|  | Ammonium formate, w-% | Furfural, w-% | Water, w-% |
| --- | --- | --- | --- |
| Aqueous phase | 25.5 | 3.0 | 71.5 |
| Organic phase |  | 0.0 |  |

Example 7

A liquid mixture of 60.01 g formic acid, 60.00 g furfural, and 30.0 g water was put in a glass vessel. 85.28 g of 26 w-% aqueous ammonia was added in to the same glass vessel by a pump within a period of 30 min. The mixture was agitated by a magnetic stirrer during alkali addition. The mixture was poured into a separation funnel. Separation into organic and aqueous phase took place after letting the filtrate stand for 5 min. and the two phases were removed into separate vessels. Samples for the analysis were taken from both phases. The analysed results are shown in Table 7.

TABLE 7

|  | Ammonium formate, w-% | Furfural, w-% | Water, w-% |
| --- | --- | --- | --- |
| Aqueous phase | 46.0 | 1.7 | 52.3 |
| Organic phase |  | 0.3 |  |

Example 8

A liquid mixture of 1040.01 g formic acid, 129.99 g furfural, and 130.0 g water was put in a glass vessel. A mixture of 1267.72 g KOH and 1901.67 g water was added into the same glass vessel by a pump within a period of 120 min. The mixture was agitated by a magnetic stirrer during alkali addition. 500 g of mixture was collected into a separate vessel. From the rest of the solution 3914.24 g of water and furfural was evaporated. The remaining liquid, 1544.95 g, was concentrated formate solution. The concentrated formate solution was mixed with the original liquid 500 g, to be as a mother liquid of a crystallization process. The mixture was analysed. The analysed results are shown in Table 8.

TABLE 8

|  | Potassium formate, w-% | Furfural, w-% | Water, w-% |
| --- | --- | --- | --- |
| Mother liquid | 79.1 | 0.4 | 20.5 |

The mother liquid was poured into a cooling vessel equipped with cooling jacket. During the crystallization the temperature of mother liquid was cooled in 6 hours from 50° C. to 20° C. by a controlled cooling profile. Crystallizer was equipped with turbine mixer with mixing velocity of 170 rpm.

A sample of produced potassium formate was dried by plotting paper and then analyzed. The furfural content in crystals was <0.01 w-%. The formed crystal is shown in FIG. 5

Example 9

A liquid mixture of 1248.38 g formic acid, 156.00 g furfural, and 556.02 g water was put in a glass vessel. 2775.93 g of 26 w-% aqueous ammonia was added into the same glass vessel by a pump within a period of 120 min. The mixture was agitated by a magnetic stirrer during alkali addition. 500 g of mixture was collected into a separate vessel. From the rest of the solution 1830.91 g of water and furfural was evaporated. The remaining liquid, 1972.31 g, was concentrated formate solution. The concentrated formate solution was mixed with the original liquid 500 g, to be as a mother liquid of a crystallization process. The mixture was analysed. The analysed results are shown in Table 9.

TABLE 9

|  | Ammonium formate, w-% | Furfural, w-% | Water, w-% |
| --- | --- | --- | --- |
| Mother liquid | 77.0 | <0.1 | 23.0 |

The mother liquid was poured into a cooling vessel equipped with cooling jacket. During the crystallization the temperature of mother liquid was cooled in 6 hours from 60° C. to 30° C. by a controlled cooling profile. Crystallizer was equipped with turbine mixer with mixing velocity of 170 rpm.

A sample of produced ammonium formate was dried by plotting paper and then analyzed. The furfural content in crystals was <0.01 w-%.

Example 10

Ammonium formate crystallization was studied from water as such and in the presence of small amount of furfural.

Crystallization experiments were carried out in a 1 liter stirred tank crystallizer. The initial ammonium formate solution was prepared by gradually adding 572.5 g 25 w % aqueous ammonia to 388.7 g 99.5 w % formic acid under reflux while mixing and cooling intensively. About 251 g of water was then evaporated from the solution at reduced pressure to concentrate the solution to about 76 w % (ref. solubility in Table 10). The temperature of the solution was adjusted to 60° C. A small amount of water (42.1 g) was then added to dissolve crystals formed during evaporation to give a stable clear solution at 60° C. The reference crystallization was without furfural. The crystallization was commenced at 60° C. with programmed cooling profile. The agitation rate was 250 rpm. The end temperature was of 30° C. and cooling time 6 h. A sample was drawn from the crystal slurry at 30° C. and filtered using glass sinter (G3). The obtained crystals were photographed by optical microscope with a 250 μm (or 200 μm) reference bar. The pictures of the crystals are presented in FIG. 7.

The slurry from the reference crystallization was heated back to 60° C. to dissolve ammonium formate and 3.8 g of furfural was added to the solution corresponding 0.5 w % in the initial mixture. Crystallization was commenced at 60° C. with equivalent cooling profile and time and agitation as in the case of pure system. The pictures of the obtained crystals are presented in FIG. 8. The crystals were yellowish due to the presence of a layer of brownish mother liquor on the surface. Small black dots on the crystal surface may be polymerized furfural. However, the crystals were more ideal in shape compared to crystals from the pure system. The average crystal size was about the same in both cases.

Table 10 shows the solubility of ammonium formate (in anhydrous form) into water (Jaroslav Nyvlt, Solid-Liquid Phase Equilibria, Elsevier Scientific Publication Co, 1977, p 193).

TABLE 10

| Temp ° C. | Solubility (1) w % | g/100 g water |
|---|---|---|
| 0 | 50.8 | 103.3 |
| 20 | 58.9 | 143.3 |
| 40 | 67.1 | 204.0 |
| 60 | 75.7 | 311.5 |
| 80 | 84.2 | 532.9 |

The invention claimed is:

1. A method for separating and recovering a formate salt from an aqueous liquid mixture containing formic acid, levulinic acid, and up to 10% by weight furfural, obtained by a degradation of biomass process, comprising:
   subjecting said mixture to liquid-liquid extraction process with an extracting agent, resulting in an organic phase comprising said extracting agent, formic acid, levulinic, acid furfural, and up to 5% by weight water, and an aqueous phase comprising water and at least one inorganic acid;
   separating said aqueous phase from said organic phase;
   separating and recovering furfural from said organic phase and recycling the aqueous phase formed in the furfural recovery back to an infeed of said organic phase;
   separating formic acid from said organic phase by distillation; and
   recovering the formic acid in a form of formate salt from said organic phase by subsequent neutralisation.

2. The method according to claim 1, further comprising recycling said extracting agent back to the liquid-liquid extraction process.

3. The method according to claim 1, further comprising recycling said aqueous phase separated from the liquid-liquid extraction back to the degradation of the biomass process.

4. The method according to claim 1, wherein the distillation comprises separating and recovering the furfural from an uppermost part of a distillation column, separating and recovering the formic acid from a middlemost part of the distillation column and separating and recovering levulinic acid from the bottommost part of the distillation column.

5. The method according to claim 1, wherein said biomass comprises cellulosic biomass material containing carbohydrates with components at least partly converted to the furfural during the degradation of said biomass process.

6. The method according to claim 1, wherein said aqueous liquid mixture comprises formic acid up to 10% by weight, levulinic acid up to 15% by weight and furfural up to 10% by weight.

7. The method according to claim 1, wherein the levulinic acid is recovered by distillation or as a salt after the neutralisation.

8. The method according to claim 1, wherein said aqueous liquid mixture to said extracting agent is at a ratio of 1:1 to 10:1.

9. The method according to claim 1, wherein the levulinic acid is recovered at a concentration of at least 50% by weight.

10. The method according to claim 1, wherein the furfural is recovered at a concentration of at least 85% by weight.

11. The method of claim 1, wherein the formate salt comprises crystal particles having an equivalent spherical diameter of at least 100 μm and a sphericity larger than 0.5.

12. The method of claim 11, wherein the formate salt is ammonium formate.

13. The method of claim 11, wherein the formate salt is potassium formate.

14. The method of claim 1, wherein the formate salt is crystallized from the mixture comprising furfural.

15. The method of claim 1, further comprising recovering levulinic acid or levulinate salt from said organic phase.

16. The method of claim 1, further comprising separating and recovering the furfural from the aqueous phase.

* * * * *

UNITED STATES PATENT AND TRADEMARK OFFICE
CERTIFICATE OF CORRECTION

PATENT NO.       : 8,492,586 B2                                                                  Page 1 of 1
APPLICATION NO.  : 12/988998
DATED            : July 23, 2013
INVENTOR(S)      : Reunanen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 269 days.

Signed and Sealed this
Eighth Day of September, 2015

Michelle K. Lee
*Director of the United States Patent and Trademark Office*